United States Patent [19]
Montealegre et al.

[11] 4,280,651
[45] Jul. 28, 1981

[54] AIR FRESHENER CARTON

[75] Inventors: James Montealegre, West St. Paul; Daniel P. Dutcher, Woodbury, both of Minn.

[73] Assignee: Champion International Corporation, Stamford, Conn.

[21] Appl. No.: 108,848

[22] Filed: Dec. 31, 1979

[51] Int. Cl.³ .................... B65D 5/38; B65D 5/36; A61L 9/04
[52] U.S. Cl. ............................... 229/20; 229/9; 239/59
[58] Field of Search ............ 229/9, 10, 19, 20, 23 BT; 239/59, 60

[56] References Cited
U.S. PATENT DOCUMENTS

| | | | |
|---|---|---|---|
| 2,256,257 | 9/1941 | Dumehart, Jr. | 229/9 UX |
| 2,277,097 | 3/1942 | Hansen | 229/9 |
| 2,361,984 | 11/1944 | Williamson | 229/19 |
| 2,998,907 | 9/1961 | Lange | 229/20 |
| 3,186,542 | 6/1965 | Greene | 229/20 X |
| 3,974,956 | 8/1976 | Delang | 229/9 X |
| 4,219,145 | 8/1980 | Jaeschke et al. | 239/59 X |

FOREIGN PATENT DOCUMENTS 121737  3/1931  Austria .
2238640  2/1975  France .

Primary Examiner—Davis T. Moorhead
Attorney, Agent, or Firm—Evelyn M. Sommer

[57] ABSTRACT

A carton for diffusing an air freshener to the atmosphere including an outer imperforate sleeve slidably receiving in nesting relation an inner sleeve housing a cake of air freshener and having a plurality of openings selectively exposed by moving the outer sleeve relative to the inner sleeve so that the air freshener can be diffused. The outer sleeve has a pair of opposed side panels defined by a series of panels hinged to each other. The last panel in each side wall series is adhesively secured to the top closure wall of the inner sleeve to preclude disassembly of the inner and outer sleeves, while permitting the openings in the inner sleeve to be selectively exposed.

4 Claims, 15 Drawing Figures

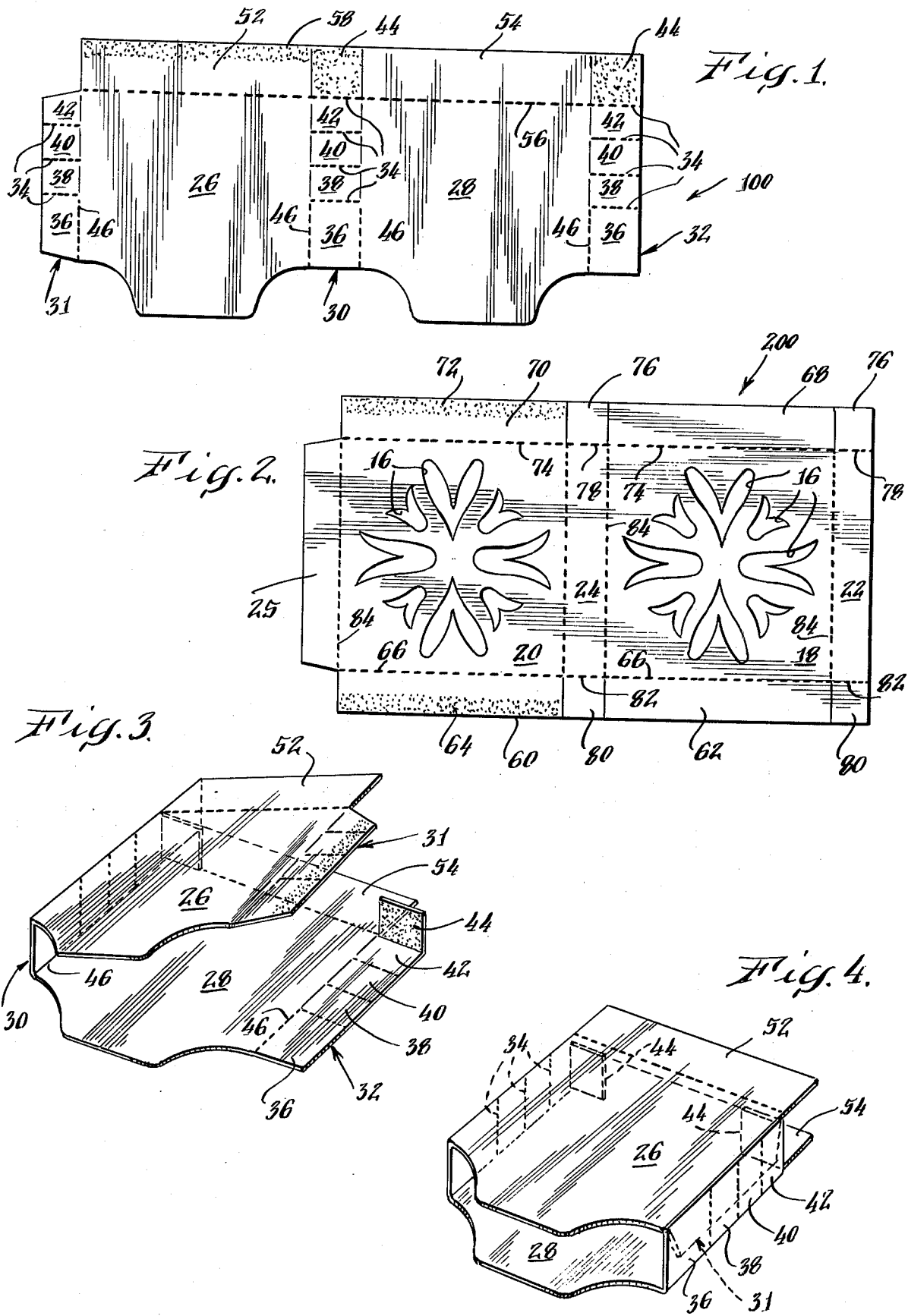

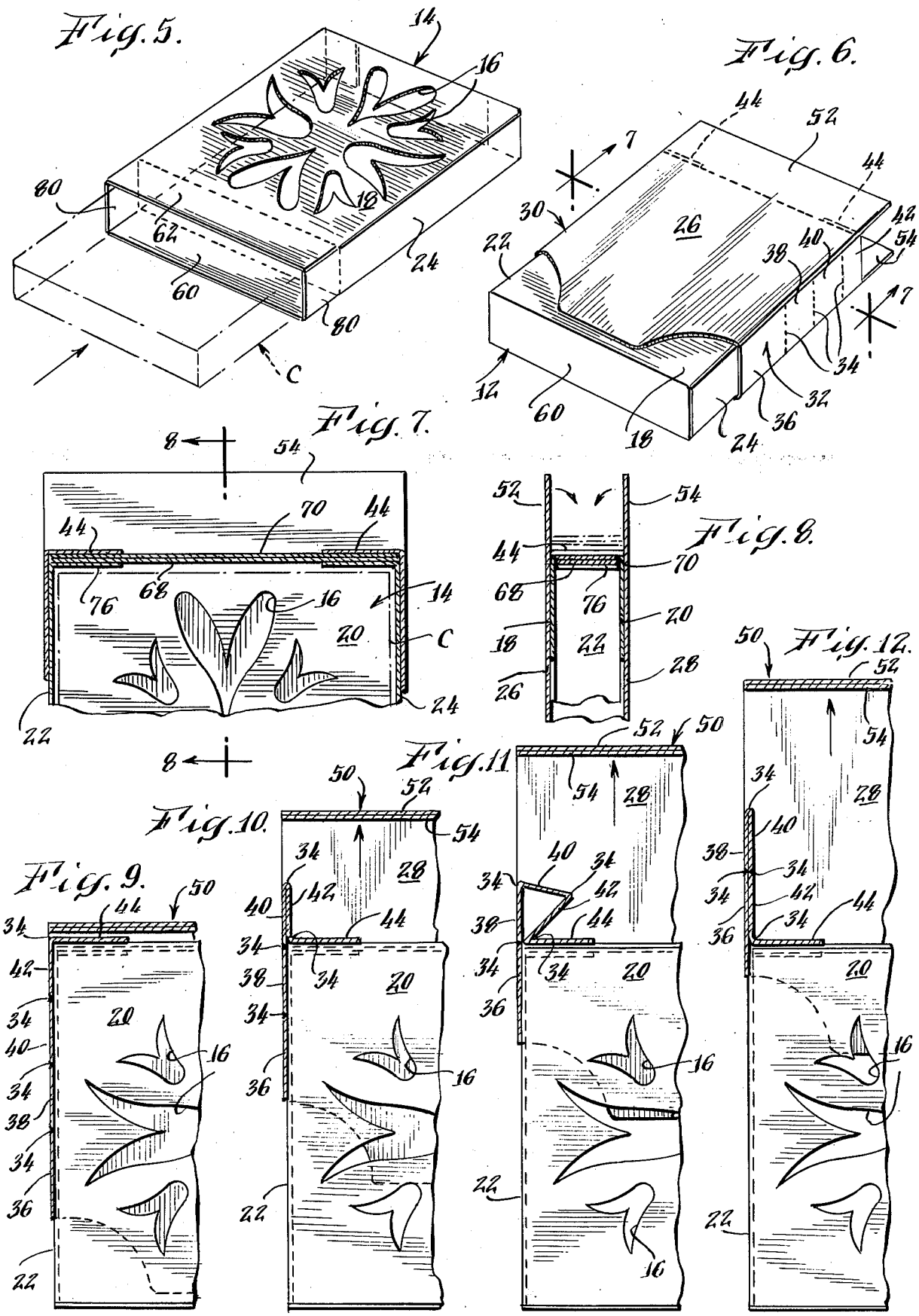

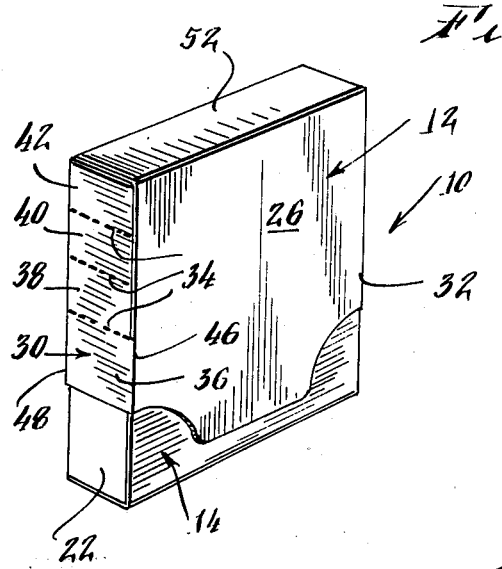
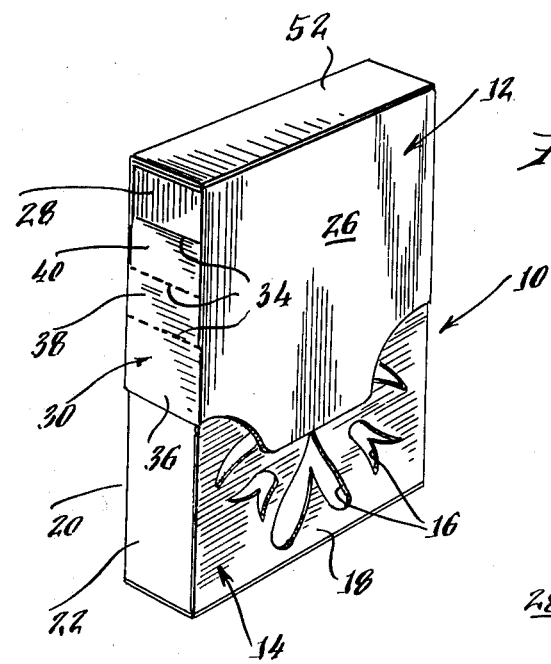
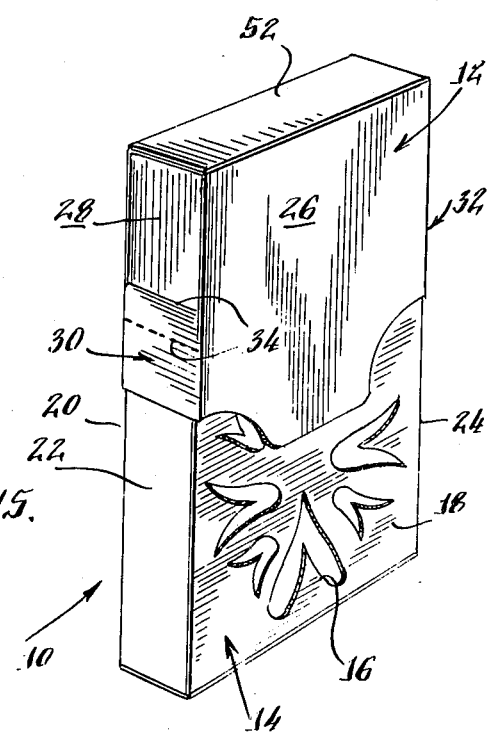

AIR FRESHENER CARTON

BACKGROUND OF THE INVENTION

1. Field of Invention

The present invention relates to cartons, and more particularly to a carton for holding an active material and controllably releasing it to the air.

2. Description of the Prior Art

There are a variety of active materials for use in household and commercial applications which it is desirable to contact with and release into the ambient air. Among these are insecticides and air fresheners which can be packaged in solid form in containers having air passages which permit release. Frequently, products of this type are packaged in containers having a plurality of openings which are closed at the time of purchase but which are opened at the time of use to allow room air to circulate over the surface of the solid active material.

In one type of carton, the openings are covered with a panel of release paper. When the consumer is ready to use the product, such as an air freshener, the release paper is peeled from the face of the container to allow room air to begin circulating through the openings. In another type of carton, the consumer activates the air freshener material by squeezing to release an encapsulated active ingredient. In yet another type of carton, holes in an outer carton wall are opened or closed by a slidable inner sheet which acts as a valve.

Molded plastic containers, usually consisting of a molded shell and a separate molded cover, have been employed to hold air freshener material. However, while molded plastic containers have an aesthetically pleasing appearance, the cost of making them is higher than might be desired. The shell and cover must be molded in separate operations and stored in unassembled form until the air freshener insert is loaded. The cover then must be glued or otherwise secured to the shell to provide a closed container. The extra time required for the separate manufacturing and assembly operations results in added manufacturing costs for the package and ultimately for the product sold therein. The fact that the molded shells and covers must be shipped and stored in their molded form will also cause increased transportation and storage costs.

In a prior patent application, U.S. Ser. No. 25,012 filed Mar. 29, 1979 entitled "CARTON WITH ADJUSTABLE AIR PASSAGES", assigned to the same assignee as the present invention, an improved package for controllably releasing active materials to the air is disclosed which has inner and outer slidable members constructed of a sheet material wherein the inner and outer members can be slidably moved between open and closed positions. The carton has a plurality of adjustable air passages and comprises: (a) a first tapered sleeve forming an outer carton unit, said first sleeve being closed at at least one end and having a plurality of spaced openings therein; and (b) a second tapered sleeve forming an inner carton unit, said second sleeve being nested within said first sleeve and being slidable between a first position and a second position, said second sleeve being closed at at least the end opposite said end closed in said first sleeve and having a plurality of spaced openings therein arranged complementarily to said spaced openings in said outer carton unit to align with the openings therein when said inner carton unit is in said first position, and to align with the spaces between said openings in said outer carton unit when said inner carton unit is in said second position.

When the openings are aligned, they permit air to circulate through the openings into the interior of the inner carton unit to permit the release or diffusion of material housed within the inner unit to the air. The tapered sleeves normally bind when moved relative to each other and when the openings are out of alignment, the diffuser is inoperative, as the openings in the inner unit are closed.

SUMMARY OF THE INVENTION

The present invention relates to an improved carton of the type having an inner and outer carton unit for use in dispensing an active material to the atmosphere.

The outer unit does not, however, contain openings, but is a solid sleeve which receives the inner unit in longitudinal, sliding engagement. The inner unit contains a plurality of openings on two facing, major panels through which air can circulate about a cake of active material, such as air freshener material. In order to diffuse the active material to the atmosphere, it is only necessary to slide the inner carton unit relative to the outer carton unit or sleeve to expose the openings to the atmosphere. When not in use, the inner carton unit is housed completely within the sleeve.

The top of the inner carton unit is adhesively connected to a plurality of hinge panels forming a portion of opposed side walls of the outer, imperforate sleeve unit. Not only can the inner carton be slid relative to the outer imperforate sleeve to expose selective openings in the inner carton to diffuse an active material without the outer and inner units becoming disassembled, but the plurality of hinge panels enable the outer imperforate carton unit or sleeve to assume a plurality of fixed intermediate positions relative to the inner sleeve for selectively uncovering some or all of the openings in the inner carton unit.

BRIEF DESCRIPTION OF THE DRAWINGS

Further objects and advantages of the invention will become apparent from the following description and claims, and from the accompanying drawings, wherein:

FIG. 1 is a top plan view of a blank for forming the outer, imperforate unit or sleeve of the carton of the present invention;

FIG. 2 is a top plan view of a blank for forming the inner carton unit or sleeve of the carton of the present invention;

FIGS. 3 to 6, inclusive, are perspective views illustrating the manner of folding and assemblying the blanks of FIGS. 1 and 2 into the carton of the present invention;

FIG. 7 is a cross sectional view taken substantially along the plane indicated by line 7—7 of FIG. 6;

FIG. 8 is a cross sectional view taken substantially along the plane indicated by line 8—8 of FIG. 7;

FIGS. 9 to 12, inclusive, are partial cross sectional views through the carton of the present invention indicating successive positions which can be assumed by the outer, imperforate sleeve relative to the inner carton unit to selectively diffuse an active material from the interior of the inner carton unit;

FIG. 13 is a perspective view of the carton of the present invention, corresponding to the position of the outer imperforate sleeve relative to the inner carton unit illustrated in FIG. 9;

FIG. 14 is a perspective view of the carton of the present invention with the outer imperforate sleeve positioned relative to the inner carton unit corresponding to FIG. 10; and FIG. 15 is a perspective view of the carton of the present invention with the outer imperforate carton sleeve positioned relative to the inner carton unit so as to fully expose the openings in the inner carton unit and corresponds to the position of the units illustrated in FIG. 12.

DETAILED DESCRIPTION OF THE PREFERRED EMBODIMENT

Referring now to the drawings in detail, wherein like numerals indicate like elements throughout the several views, the carton 10 of the present invention includes an outer, imperforate sleeve member 12 slidably receiving an inner carton sleeve member 14. Inner carton member 14 includes a plurality of openings 16 on a front and rear parallel, major panel 18 and 20. Housed within the inner carton unit 14 between panels 18 and 20 is a cake of active material C, such as an air freshener.

Inner carton unit 14 also includes opposed side walls 22 and 24 connecting the front and rear panels 18 and 20. The outer imperforate sleeve unit 12 of carton 10 is slidably received over the panels 18, 20, 22 and 24 and has correspondingly mating, overlying, panels 26, 28, 30 and 32. The side wall panels 30 and 32 of the outer imperforate sleeve 12 are divided by hinge lines 34 into five connected panels 36, 38, 40, 42, and 44. The panels 36 remain connected or attached to the front and rear panels 26 and 28 by vertical score lines 46 and 48, respectively. The remaining four panels on each side wall 30, 32, namely panels 38, 40, 42 and 44, are cut along their lateral edges and are not connected to the front or rear panels 26 and 28, respectively. Rather, as shown in FIGS. 9 to 12, the panels can freely pivot relative to each other making flexible side walls, and the topmost panel 44 on each side wall 30, 32 is adhesively connected to the top closure wall 70 of the inner carton member 14.

When the front and rear panels 26 and 28 of the outer, imperforate sleeve 12 are raised and slid relative to the inner carton unit 14 in the direction of the arrow indicated in FIGS. 9 to 12, inclusive, each panel 44, 42, 40, and 38 is selectively pivoted about its adjacent hinge line 34 to permit the inner carton unit 14 to be disposed at various extended positions relative to the imperforate outer sleeve 12 to selectively expose certain ones, more or less, of the opening 16 to the atmosphere, so that air can circulate about the active material within the interior of the inner carton unit 14 and diffuse it to the atmosphere. The hinge arrangement described also precludes the inner carton unit 14 from becoming disassembled from the outer imperforate sleeve 12.

The outer imperforate sleeve 12 is formed from a unitary, paperboard blank 100, illustrated in FIG. 1.

The blank 100 includes front and rear panels 26, 28 which are joined together by a side wall panel 30. The second side wall panel 32 extends from the opposite edge of rear wall panel 28. A third side wall panel 31 containing corresponding panels 36, 38, 40 and 42 extends outwardly from the free edge of the front wall panel 26. Panel 31 does not contain the panel 44 which is adhesively secured to the top wall of the inner carton unit 14. Side wall panel 32 is overlapped with panel 31 and the outer surface of panel 31 adhesively secured to the inner surface of panel 32 as illustrated in FIGS. 3 and 4 to form a tubular member prior to closing its top to complete the outer imperforate sleeve unit 12. In securing panel 31 to panel 32, the hinge lines 34 are aligned as well as the panels 36 to 42. Also secured to the top edges of front and rear panels 26 and 28 are top, rectangular closure panels 52 and 54 secured to the respective front and rear panel 26, 28 by a score line 56.

As illustrated in FIGS. 3 and 4, the blank 100 is folded about vertical hinge lines 46 so that the panels 26 and 28 extend parallel to each other. Then the panels 32 and 31 are bent ninety degrees with respect to panels 26 and 28 and adhesively secured as described hereinbefore. In order to complete the fabrication of the imperforate outer sleeve 12, the top glue panels 44 of the side walls 30, 32 are bent ninety degrees to overly the interior of the outer imperforate sleeve. Then, closure panels 52 and 54 are bent ninety degrees about their respective score lines 56 and overlapped, with the glue area 58 on panel 52 adhered to the outer surface of panel 54 forming a closure wall 50.

The inner carton unit 14 is also formed from a unitary, planar paperboard blank 200, illustrated in FIG. 2.

The blank 200 includes square front and rear panels 18 and 20 containing corresponding openings 16. The panels 18 and 20 are connected by a rectangular side wall panel 24. Extending outwardly of the front panel 18 is the side panel 22. Extending outwardly from the free edge of the back or rear panel 20 is another side glue panel 25. Each of the panels 22, 24, and 25 are connected to its adjacent lateral panel by a vertical score line 84.

Extending upwardly from the front and rear panels 18 and 20, respectively, are rectangular panels 68 and 70, respectively, connected to the panels by a horizontal score line 74. Similarly, a rectangular panel 62 and 64 is foldably connected to the bottom edge of the panels 18 and 20 and is foldable about a score line 66. The rectangular panel 60 includes an adhesive or glue area 64, while the rectangular panel 70 includes an adhesive or glue area 72.

A tab 76 is foldably connected by a score line 78 to the top edge of both side panels 22 and 24. Similarly, a tab 80 is connected by a score line 82 to the bottom edge of each of the side panels 22 and 24.

As illustrated in FIG. 5, blank 200 is formed into inner carton unit 14 by folding the panels 18 and 20 about vertical score lines 84 until they lie parallel to each other. Panel 22 is also folded ninety degrees about vertical score line 84 while panel 25 is folded about its vertical score line 84. Side wall panel 22 is overlapped with panel 25 and is adhesively secured thereto. The ends of the inner carton unit 14 are then closed by bending tab 76 downwardly and tabs 80 upwardly about their respective score lines 78 and 82. Panels 68 and 70 are then bent ninety degrees about score line 74 and overlapped with the adhesive surface 72 on the interior surface of panel 70 adhesively secured to the outer surface of rectangular panel 68. Similarly, panel 60 is overlapped onto panel 62 and the adhesive surface 64 on the inner surface of rectangular panel 60 adhesively secured to the outer surface of panel 62. The ends of the blank 200 are closed after a cake C of active material, such as air freshener material, is disposed between panels 18 and 20 beneath opening 16.

Once the inner carton unit 14 is assembled, the outer imperforate sleeve 12 is slid over the inner unit 14 as illustrated in FIG. 6 until the openings 16 are disposed beneath panels 26 and 28. Then, panels 52 and 54 are overlapped with the adhesive area 58 secured to the outer surface of panel 54 to form the closure wall 50 which limits relative axial movement of the inner and outer units. Prior to overlapping and closing panels 52 and 50 to form closure wall 50, the adhesive surface on tabs 44 are adhesively connected, as indicated in FIGS. 7 and 8, to the top surface of the outer panel 70 of the inner carton unit 14.

As illustrated in FIGS. 9 to 15, inclusive, by pulling the inner carton unit 14 away from the top closure wall 50 of outer imperforate sleeve 12, the side walls 30 and 32 have their hinged panels 44-38, inclusive, progressively pivoted and pulled downwardly away from the closure wall 50 enabling openings 16 in the front and rear panels 18 and 20 of the inner carton unit 14 to be successively exposed so that air from the atmosphere can circulate into the interior of the inner carton unit 14 and diffuse the active material therefrom. The connection of the side walls of the outer carton unit to the bottom wall of the inner carton unit precludes their disassembly.

What is claimed as new is:

1. A carton comprising:
    a first imperforate outer sleeve forming an outer carton unit having a pair of opposed major panels connected by a pair of opposed foldable side wall panels,
    a second sleeve forming an inner carton unit having a pair of opposed major panels parallel to the major panels of the first sleeve and connected by a pair of opposed side wall panels,
    said second sleeve being nested within said first sleeve and being slidable relative thereto,
    said second sleeve being closed by top and bottom closure walls at opposite ends and having a plurality of openings in at least one major panel thereof, and
    flexible means connecting said opposed side wall panels of said outer carton unit to the top closure wall of said inner carton unit for preventing said inner and outer carton units from being disassembled while permitting them to slide relative to each.

2. A carton in accordance with claim 1 wherein said flexible means includes
    a plurality of panels hingedly connected in series to each other and to a side wall panel of said outer carton unit,
    one of said panels being adhesively secured to the top closure wall of said inner carton unit.

3. A carton in accordance with claim 2 wherein the last one of said hinged panels in said series is adhesively secured to said top closure wall of said inner carton unit.

4. A carton in accordance with claim 3 wherein said first imperforate outer sleeve includes a sealed top closure for abutment with the top closure wall of said inner carton unit.

* * * * *